(12) United States Patent
Bogdanovich et al.

(10) Patent No.: US 11,587,659 B2
(45) Date of Patent: Feb. 21, 2023

(54) PILL PACK PACKAGING

(71) Applicant: CIPHER SKIN, Denver, CO (US)

(72) Inventors: Phillip Bogdanovich, Evergreen, CO (US); Craig Weller, Evergreen, CO (US); Shaka Joaquin Doyle Bahadu, Emeryville, CA (US)

(73) Assignee: CIPHER SKIN, Denver, CO (US)

( * ) Notice: Subject to any disclaimer, the term of this patent is extended or adjusted under 35 U.S.C. 154(b) by 250 days.

(21) Appl. No.: 16/825,938

(22) Filed: Mar. 20, 2020

(65) Prior Publication Data

US 2020/0303051 A1   Sep. 24, 2020

Related U.S. Application Data (60) Provisional application No. 62/820,879, filed on Mar. 20, 2019.

(51) Int. Cl.
| | |
|---|---|
| *G16H 20/13* | (2018.01) |
| *A61J 1/03* | (2023.01) |
| *A61J 7/02* | (2006.01) |
| *H04W 12/63* | (2021.01) |

(52) U.S. Cl.
CPC ............ *G16H 20/13* (2018.01); *A61J 1/035* (2013.01); *A61J 7/02* (2013.01); *A61J 2200/30* (2013.01); *H04W 12/63* (2021.01)

(58) Field of Classification Search
CPC ....... G16H 20/13; A61J 2200/30; A61J 1/035; A61J 7/02
See application file for complete search history.

(56) References Cited

U.S. PATENT DOCUMENTS

| | | | |
|---|---|---|---|
| 2005/0122219 A1 | 6/2005 | Petersen et al. | |
| 2007/0246396 A1 | 10/2007 | Brollier | |
| 2009/0109800 A1 | 4/2009 | Kimel et al. | |
| 2009/0277815 A1* | 11/2009 | Kohl | A61J 1/035 700/235 |
| 2013/0222135 A1* | 8/2013 | Stein | A61J 7/0436 222/23 |
| 2013/0285681 A1 | 10/2013 | Wilson et al. | |
| 2016/0132661 A1 | 5/2016 | Dixit et al. | |
| 2017/0046501 A1 | 2/2017 | Coleman et al. | |
| 2017/0248401 A1 | 8/2017 | Isom et al. | |
| 2018/0125761 A1* | 5/2018 | Conlon | B65B 65/08 |
| 2019/0244510 A1* | 8/2019 | Mehregany | A61J 1/035 |

FOREIGN PATENT DOCUMENTS

EP      2269561 A1    1/2011

OTHER PUBLICATIONS

Brath, Helmut, et al., "Mobile Health (mHealth) Based Medication Adherence Measurement—A Pilot Trial Using Electronic Blisters in Diabetes Patients," British Journal of Clinical Pharmacology, May 16, 2013, pp. 47-55.

\* cited by examiner

*Primary Examiner* — Timothy R Waggoner
(74) *Attorney, Agent, or Firm* — Lorenz & Kopf, LLP (57) ABSTRACT

Pill pack packaging that monitors and reports on pill compliance is disclosed. The pill pack packaging includes a circuit disposed on the cover of pill receptacles. A processor monitors the changes in electrical signals from the circuit. When the electrical signals change, the processor records the time and date. The processor may also report the time and date of pill receptacle opening to a mobile device via wireless transmission. The device may also be capable of providing alerts regarding lack of compliance or loss of the pill pack.

18 Claims, 4 Drawing Sheets

PILL PACK PACKAGING

RELATED PATENTS

This application claims priority to U.S. Patent Application No. 62/820,879, filed on Mar. 20, 2019, which is incorporated by reference as if fully set forth herein.

FIELD OF THE INVENTION

Embodiments disclosed herein relate to a system and method for monitoring medication (e.g., pill) usage. Certain embodiments disclosed herein relate to a pill packaging system used to monitor medication (pill) usage through the use of thin film circuits.

BACKGROUND

A wide range of studies have shown that people struggle to take medication—even lifesaving drugs such as cancer medication—on a consistent basis. The rate of successful compliance with a medication schedule varies significantly depending on the number of daily doses. As you increase the number of daily doses or include multiple medications, there is a substantial drop-off in compliance.

With a single daily dose of a medication, the mean compliance rate is typically around 79%. If the same medication requires two doses per day, the patient will follow the dosing schedule around 69% of the time. If the patient has to remember four different doses of medication in a day, such as breakfast, lunch, dinner, and bedtime, the compliance rate drops to around 51%. In conditions where patients have to remember to not just take a medication but to also take it at a specific time, compliance also drops significantly, to a mean of around 59%.

The lack of compliance presents a significant risk to global healthcare. Even the better medications in the world are less effective if people fail to take them. Detection of adequate compliance with medication schedules is crucial for effective treatment. Numerous counts, and therapeutic outcomes. These methods, however, involve significant time delays and are often subject to significant reliability issues.

Thus, there is a need to ensure adequate compliance from day to day throughout a patient's treatment regimen. A direct method of monitoring compliance and providing reminder-based support may be more effective at producing positive outcomes.

Low medication compliance rates may also pose a significant challenge to researchers. It may be impossible to assess the efficacy of a treatment regimen if it cannot be known with any certainty that a medication is actually being taken as prescribed. Direct monitoring and patient support may provide a critical mechanism for increased certainty in research and drug trial data collection.

There have been attempts to provide tracking systems for drug (medication). These systems, however, are often large container systems and/or cumbersome to implement. For example, container systems have been designed to be used with printing conductive ink onto packaging. These systems are designed to print onto paper backing and/or direct print, which may limit pack (e.g., pill pack) production capability to organizations that have the ability to print on their own.

Based on the foregoing, current technologies and processes associated with ensuring compliance with treatment regimens may be enhanced and improved upon. In particular, such enhancements and improvements may facilitate easier tracking, more accurate data, faster monitoring capabilities, increased compliance with treatment regimens, improved health outcomes, among other benefits.

SUMMARY

Pill pack packaging that monitors and reports on pill compliance is disclosed. The pill pack packaging may include a circuit disposed on the cover of pill receptacles. A processor may monitor electrical signals from the circuit and the changes in electrical signals from the circuit. When the electrical signals change, the processor may record the time and date of such changes. In certain embodiments, the processor may also report the time and date of pill receptacle opening to a mobile or other device, such as via wireless transmission. The device may also be capable of providing alerts regarding lack of compliance or loss of the pill pack.

In an embodiment, a pill package enclosure is disclosed. The pill package enclosure may include a membrane for covering one or more pill pouches in a pill pack. The pill package enclosure may also include a circuit, which may include a processor and a battery. In certain embodiments, a portion of the circuit may cover a pill pouch of the pill pouches. In certain embodiments, the portion of the circuit covering the pill pouch may be coupled to the processor and the battery. The processor may be configured to monitor removal of a pill from the pill pouch by assessing changes in electrical signals from the portion of the circuit covering the pill pouch.

In another embodiment, a method for monitoring medication usage is disclosed. The method may include providing a pill pack having a pill disposed within a pill pouch and a membrane that covers the pill pouch. The method may also include monitoring a circuit that covers a portion of the pill pouch for a change in an electrical signal. In certain embodiments, the change in the electrical signal may occur when the pill pouch is opened. The method may also include recording a date and a time the pill pouch was opened by using a processor, and transmitting a signal indicating the opening of the pill pouch to a mobile device. The method may also include providing a compliance schedule to the processor, and utilizing the processor to compare the date and time that the pill pouch was opened to the compliance schedule to determine whether a user complied with the compliance schedule.

In a further embodiment, a monitored pill pack is disclosed. The monitored pill pack may include a pill pack having a pill well. The monitored pill pack may also include a cover disposed on the pill well and a circuit configured to monitor opening of the cover. The monitored pill pack may also include a processor to record a date and a time that the cover is opened.

BRIEF DESCRIPTION OF THE DRAWINGS

Features and advantages of the methods and apparatus described herein will be more fully appreciated by reference to the following detailed description of presently preferred but nonetheless illustrative embodiments when taken in conjunction with the accompanying drawings in which.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form illustrated, but on the contrary, the intention is to cover all modifications, equivalents and alternatives falling within the spirit and scope of the present disclosure as defined by the appended claims. The headings used herein are for organizational purposes only and are not meant to be used to limit the scope of the description. As used throughout this application, the word "may" is used in a permissive sense (i.e., meaning having the potential to), rather than the mandatory sense (i.e., meaning must). Similarly, the words "include," "including," and "includes" mean including, but not limited to. Additionally, as used in this specification and the appended claims, the singular forms "a", "an", and "the" include singular and plural referents unless the content clearly dictates otherwise. The term "coupled" means directly or indirectly connected.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

DETAILED DESCRIPTION OF EMBODIMENTS

The following examples are included to demonstrate preferred embodiments. It should be appreciated by those of skill in the art that the techniques disclosed in the examples which follow represent techniques discovered by the inventor to function well in the practice of the disclosed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosed embodiments.

This specification includes references to "one embodiment" or "an embodiment." The appearances of the phrases "in one embodiment" or "in an embodiment" do not necessarily refer to the same embodiment, although embodiments that include any combination of the features are generally contemplated, unless expressly disclaimed herein. Particular features, structures, or characteristics may be combined in any suitable manner consistent with this disclosure.

Certain embodiments described herein utilize a flexible conductive mesh coupled to pill packs (e.g., medicine pill packs) to provide tracking and monitoring of the pill packs and contents within the pill packs (e.g., pills or medication).

Certain embodiments described herein enable pill packs (e.g., medicine pill packs) to be provided with one or more of the following features:

1) Determination of when pills are removed from a pill pack (and possibly consumed);
2) Determination of an individual having the pill pack;
3) Determination of a location of an individual taking the pill(s) from the pill pack; and
4) Determination of the duration between drug administrations (e.g., duration between taking pills from the pill pack).

These features may provide systems and methods to effectively track drug (e.g., pill) consumption and monitor for compliance in taking the drugs by the individual. Embodiments described herein may provide drug (e.g., pill) containers that are inexpensive and easily deployable.

In certain embodiments, as described herein, pill (medication) packs are capable of determining where the medication is being accessed. In some embodiments, the pill packs are capable of providing determined data to a phone or other mobile device via, for example, syncing using Bluetooth, other NFC communication, and/or other communication technologies. Embodiments of pill packs described herein may be used in drug compliance and monitoring and/or narcotics fraud prevention (including narcotics and general medication theft or fraud deterrent).

Figure 1:
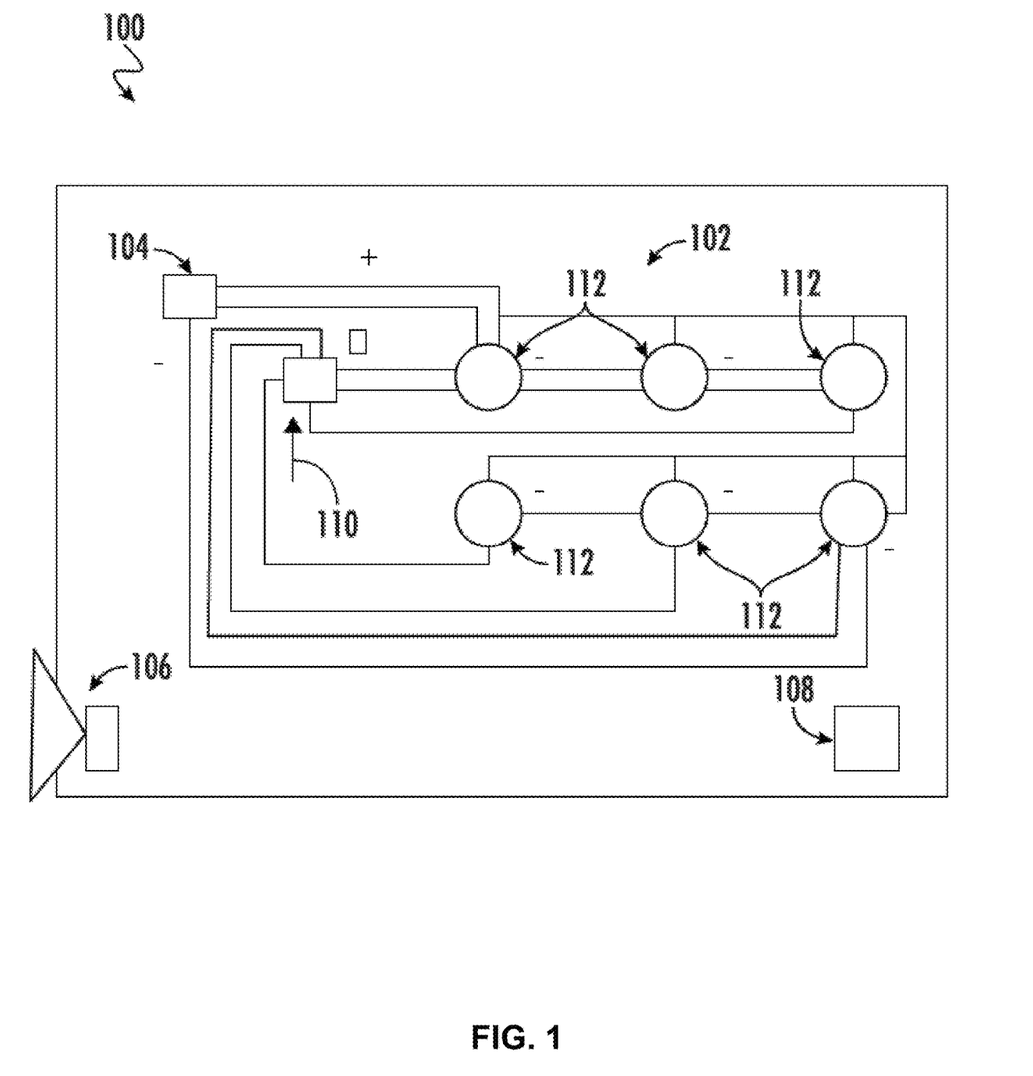
FIG. 1 depicts a representation of an embodiment of a pill pack.

FIG. 1 depicts a representation of an embodiment of pill pack 100. Pill pack 100 may include, be included as part of, packaging for pills or other medication. Pill pack 100 may also be a pill organizer. In certain embodiments, pill pack 100 includes circuit 102. Circuit 102 may be a printable circuit. In certain embodiments, circuit 102 is printed on a thin membrane. The thin membrane may be built to design specifics for pill (medication) packaging. For example, the thin membrane may be built to design specifics such as, but not limited to, transparency, breathability, rubberization, and/or heat responsiveness. The thin membrane (with circuit 102 printed on the membrane) may be deliverable in sets of determined numbers and/or may be machine loadable. For example, a set of thin membranes and circuits 102 may be transported in a canister that is machine loadable into an automated pack production system. The thin membrane (along with circuit 102 printed on the membrane) may be used as a backing for pill packaging (e.g., the backing of pill pack 100). The backing of the pill packaging may be used to access pills from pill pack 100. Thus, the thin membrane may be the surface through which a patient removes pills from pill pack 100.

In certain embodiments, circuit 102 includes battery 104 and/or other power source. Battery 104 may be a flexible battery. For example, battery 104 may be a plastic composite battery or another battery that is combustion resistant, inexpensive to manufacture, thin, and/or lightweight.

In certain embodiments, circuit 102 includes Bluetooth (BT) transmitter 106 or any other desired transmitter and/or receiver. BT transmitter 106 may provide pill pack 100 with an ability to communicate with user-specified devices such as a mobile phone or other mobile device. Generally, BT transmitter 106 is used for communication between pill pack 100 and an external user and/or external device. In some embodiments, pill pack 100 may communicate via BT transmitter 106 to ensure medication in the pill pack is taken by an appropriate individual (identified by his/her mobile device) under appropriate conditions. BT transmitter 106 may also be utilized for diagnostic purposes to indicate if there is a failure or other error with pill pack 100.

Figure 2:
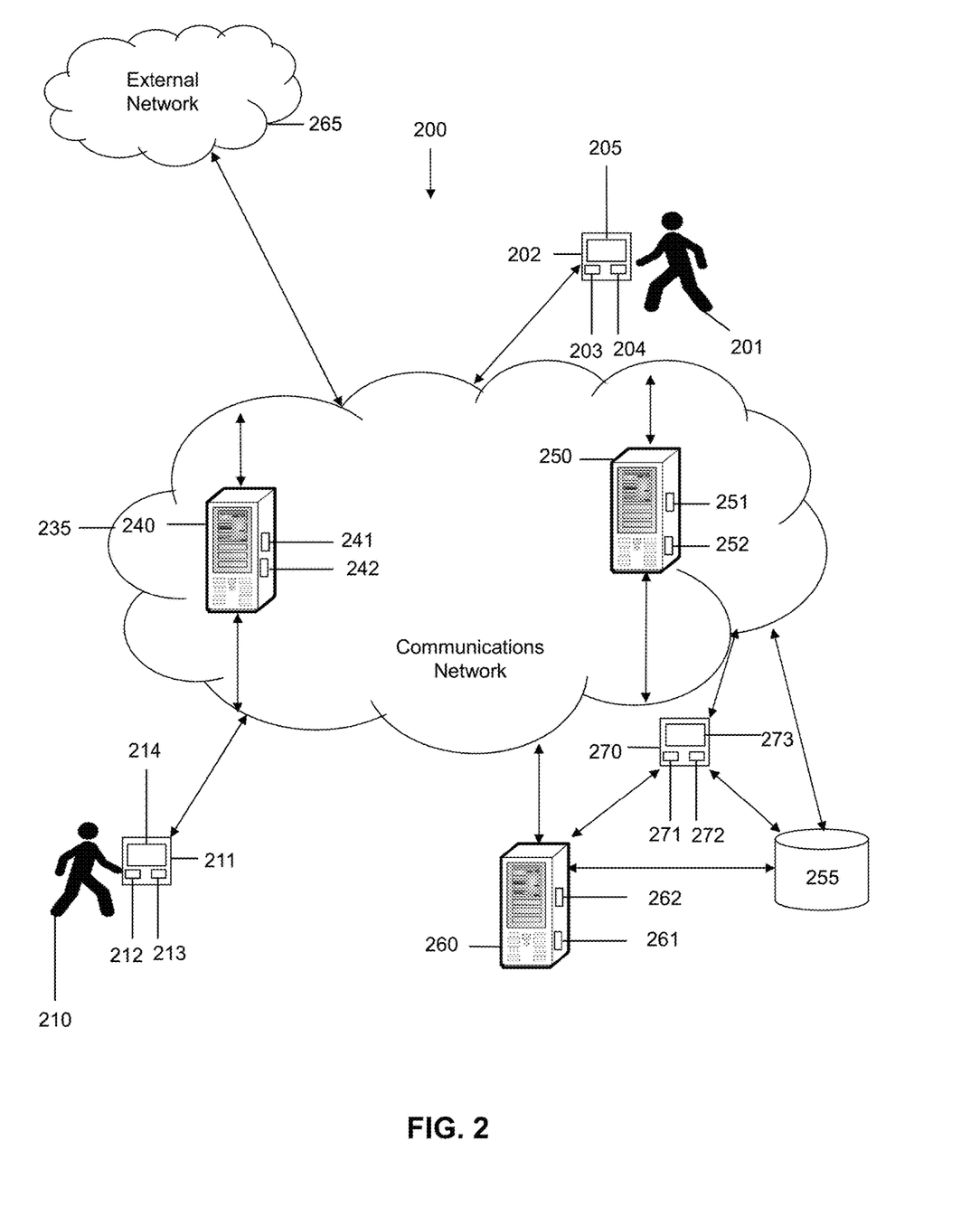
FIG. 2 is a schematic diagram of a system that may be utilized to facilitate the operation of the pill pack according to an embodiment of the present disclosure.

In certain embodiments, circuit 102 includes NFC (Near Field Communication) transmitter 108. NFC transmitter 108 may be used to provide initial pairing between pill pack 100 and a mobile device. Synchronization using NFC transmitter 108 may allow for the creation of a unique identifier for pill pack 100 such that the pill pack can be registered to a specific mobile device (e.g., the pill taker's mobile device, such as first user device 202 and/or second user device 210). In some embodiments, NFC transmitter 108 may be used for secondary purposes such as ownership determination in the event of pill pack 100 becomes lost or stolen.

In certain embodiments, circuit 102 includes processor 110. Processor 110 may be used to control and monitor circuit 102 and provide communications through either BT transmitter 106 or NFC transmitter 108. Processor 110 may be provided power by battery 104. In some embodiments, processor 110 includes or is coupled to memory (e.g., RAM memory). Memory associated with processor 110 may be numerically coded for a type of drug in pill pack 100. Processor 110 may share the numerical coding with a mobile device when pill pack 100 and the mobile device are synchronized as described herein. The mobile device may identify pill pack 100 based on the identification of the medication (e.g., drugs or pills) associated with the pill pack. The mobile device may further confirm the drug and the patient (individual) associated with the mobile device to ensure that pill pack 100 has been assigned to the correct patient.

In certain embodiments, circuit 102 includes one or more pill pouch covers 112 coupled to processor 110. Pill pouch covers 112 may be portions of circuit 102 overlying pill pouches within pill pack 100. For example, pill pouch covers 112 may be covers for blister pack cells in pill pack 100. When a pill is removed from pill pack 100, the pill may be removed through pill pouch cover 112. For example, the pill may be pushed through pill pouch cover 112 or the cover may otherwise be manipulated to allow the pill to be removed from pill pack 100. Manipulation of pill pouch cover 112 to remove the pill may affect (e.g., cause disruption in) circuit 102. Changes in signal (e.g., power signals) when pill pouch covers 112 are manipulated may be recorded using processor 110. Processor 110 may record additional information at the time pill pouch cover 112 is manipulated to remove the pill. For example, information such as, but not limited to, location of pill pack 100, mobile device synced with pill pack 100, identification of pill pouch cover manipulated, etc. In some embodiments, location information is recorded using GPS information accessed from the mobile device synced to pill pack 100. In some embodiments, pill pack 100 may include a GPS receiver that provides location information.

As described above, processor 110 may record events associated with pill pack 100 (e.g., monitoring of events associated with covers 112 in circuit 102) while being connected to a mobile device of the patient associated with the pill pack to receive data associated with the mobile device. As such, processor 110 may provide monitoring and/or determination of information associated with pill pack 100 and its identified user (e.g., the patient). Information that may be monitored and/or determined for pill pack 100 may include, but not be limited to, identification of owner of pill pack 100, location(s) and time(s) of pill(s) being removed from the pill pack, relative frequency of medication consumption, type of medication being consumed, identification of pill pouches being utilized, lot number of medication being consumed, length of time medication in possession of patient, expiration date of the medication, and type of medication in the pill pack.

In some embodiments, processor 110 provides data analysis to generate one or more items of information described above and then provides the information to a remote entity (e.g., medical professionals, healthcare providers, legal guardians, etc.). In some embodiments, processor 110 may provide raw data to a remote processor, which may then provide data analysis to generate the information. Processor 110 may provide the analyzed or raw data to a remote location by, for example, transferring data to the mobile device, which then transfers the data to the remote location.

The above-described information generated for pill pack 100 may be used, for example, to determine who is taking medication and how frequently the medication is being taken. An observer (e.g., medical professional or healthcare provider) may use these determinations to then determine if the patient is compliant with a prescribed regimen for the medication associated with the pill pack.

In some embodiments, processor 110 may include an error beacon protocol. For example, an error beacon may be either an app-based error protocol (e.g., via crowd sourcing similar to Tile) or hardware-based error protocol (e.g., via on-board cellular radio transmission). Providing an error beacon signal using the error beacon protocol may provide alerts to third parties (e.g., medical providers) under specific conditions that may require alerts. For example, alerts may be provided when pill pack 100 is opened and the pill pack is not in the proximity of the registered owner (e.g., not in proximity of registered patient's mobile device), which may indicate theft or loss of the pill pack.

In certain embodiments, the pill pack 100 and/or any of the componentry of FIG. 1 may be communicatively linked with a system 200 and/or incorporated into the system 200, as shown in FIG. 2. The system 200 may be configured to perform any of the functionality performed by the pill pack 100. Additionally, the system 200 may be configured to perform operations and/or functionality offloaded by the pill pack 100 to the system 200. For example, in certain instances, the computing, storage, and/or other resources of the pill pack 100 may be overloaded or may be nearing a threshold level that warrants offloading operations and functionality to the system 200 to assist the pill pack 100 in completing various operations and to increase performance of the pill pack 100. Notably, any of the components of the pill pack 100 may be configured to communicate with any of the components of the system 200, such as via a wired connection, wireless connection, any other type of connection, or a combination thereof. In certain embodiments, the system 200 may include the pill pack 100.

The system 200 may be configured to support, but is not limited to supporting, monitoring applications and services, pill tracking applications and services, pill package tracking applications and services, sensor-based applications and services, electrical signal monitoring applications and services, wearable device applications and services, health monitoring applications and services, communication applications and services, alert applications and services, data and content services, data aggregation applications and services, big data technologies, data synthesis applications and services, data analysis applications and services, computing applications and services, cloud computing services, internet services, satellite services, telephone services, software as a service (SaaS) applications, mobile applications and services, and any other computing applications and services. The system may include a first user 201, who may utilize a first user device 202 to access data, content, and applications, or to perform a variety of other tasks and functions. In certain embodiments, the first user 201 may be a user that is seeking to monitor their own compliance with a treatment regimen, such as a treatment regiment involving taking pills to treat a medical or other condition.

The first user device 202 utilized by the first user 201 may include a memory 203 that includes instructions, and a processor 204 that executes the instructions from the memory 203 to perform the various operations that are performed by the first user device 202. In certain embodiments, the processor 204 may be hardware, software, or a combination thereof. The first user device 202 may also include an interface 205 (e.g. screen, monitor, graphical user interface, audio device interface, etc.) that may enable the first user 201 to interact with various applications executing on the first user device 202, to interact with various applications executing within the system 200, and to interact with the system 200 itself. In certain embodiments, the first user device 202 may be a computer, a laptop, a tablet device, a phablet, a server, a mobile device, a smartphone, a smart watch, and/or any other type of computing device. Illustratively, the first user device 202 is shown as a mobile device in FIG. 2. The first user device 202 may also include a global positioning system (GPS), which may include a GPS receiver and any other necessary components for enabling GPS functionality, accelerometers, gyroscopes, sensors, and any other componentry suitable for a mobile device. In certain embodiments, the first user device 202 may be configured to include any number of sensors, such as, but not limited to, temperature sensors, pressure sensors, motion sensors, light sensors, oxygen sensors, heart rate sensors, touch sensors, proximity sensors, gas sensors, acoustic sensors, chemical sensors, acceleration sensors, humidity sensors, moisture sensors, presence sensors, force sensors, any type of sensors, or a combination thereof. In certain embodiments, the first user device 202 may be configured to communicate with any of the components of the system 200 and/or assist with any of the operations of the system 200.

In addition to the first user 201, the system 200 may include a second user 210, who may utilize a second user device 211 to access data, content, and applications, or to perform a variety of other tasks and functions. As with the first user 201, the second user 210 may be a user that is seeking to determine if they are effectively following a treatment regimen. However, in certain embodiments, the second user 210 may be a physician that is treating the first user 201, a family member that is monitoring the first user 201, and/or any other type of user. Much like the first user 201, the second user 210 may utilize second user device 211 to access an application (e.g. a browser or a mobile application) executing on the second user device 211 that may be utilized to access web pages, data, and content associated with the system 200. The second user device 211 may include a memory 212 that includes instructions, and a processor 213 that executes the instructions from the memory 212 to perform the various operations that are performed by the second user device 211. In certain embodiments, the processor 213 may be hardware, software, or a combination thereof. The second user device 211 may also include an interface 214 (e.g. a screen, a monitor, a graphical user interface, etc.) that may enable the second user 210 to interact with various applications executing on the second user device 211, to interact with various applications executing in the system 200, and to interact with the system 200. In certain embodiments, the second user device 211 may be a computer, a laptop, a tablet device, a phablet, a server, a mobile device, a smartphone, a smart watch, and/or any other type of computing device. Illustratively, the second user device 211 may be a computing device in FIG. 2. The second user device 211 may also include any of the componentry described for first user device 202. The second user device 211 may similarly be configured to communicate with any of the components of the system 200 and/or assist with any of the operations of the system 200.

In certain embodiments, the first user device 202 and the second user device 211 may have any number of software applications and/or application services stored and/or accessible thereon. For example, the first and second user devices 202, 211 may include applications for determining if a pill has been removed from a pill pouch, applications for determining compliance with a compliance schedule and/or treatment regiment, applications for determining and analyzing conditions associated with monitored objects and/or physical structures, determining and analyzing health conditions, applications for determining and analyzing the physiological status of a user, applications for generating alerts, applications for analyzing and interpreting sensor data, artificial intelligence applications, machine learning applications, big data applications, applications for analyzing data, applications for integrating data, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 201, 210 to readily interact with the software applications.

The software applications and services may also be utilized by the first and second users 201, 210 to interact with any device in the system 200, any components of the pill pack 100, any network in the system 200, or any combination thereof. For example, the software applications executing on the first and second user devices 202, 211 may be applications for receiving data, applications for monitoring compliance with treatment regimens and/or compliance schedules, applications for storing data, applications for analyzing sensor data, applications for determining health conditions, applications for determining how to respond to a health condition, applications for determining a physiological status of a user, applications for determining how to respond to an environmental condition (e.g. an environmental condition that may affect the first user 201), applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first and second user devices 202, 211 may include associated telephone numbers, internet protocol addresses, device identities, or any other identifiers to uniquely identify the first and second user devices 202, 211 and/or the first and second users 201, 210. In certain embodiments, location information corresponding to the first and second user devices 202, 211 may be obtained based on the internet protocol addresses, by receiving a signal from the first and second user devices 202, 211, or based on profile information corresponding to the first and second user devices 202, 211.

The system 200 may also include a communications network 235. The communications network 235 of the system 200 may be configured to link each of the devices in the system 200 to one another and/or to the pill pack 100. For example, the communications network 235 may be utilized by the first user device 202 to connect with other devices within or outside communications network 235. Additionally, the communications network 235 may be configured to transmit, generate, and receive any information and data traversing the system 200. In certain embodiments, the communications network 235 may include any number of servers, databases, or other componentry, and may be controlled by a service provider. The communications network 235 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. Illustratively, server 240 and server 250 are shown as being included within communications network 235.

Notably, the functionality of the system 200 may be supported and executed by using any combination of the servers 240, 250, and 260. The servers 240, and 250 may reside in communications network 235, however, in certain embodiments, the servers 240, 250 may reside outside communications network 235. The servers 240, and 250 may be utilized to perform the various operations and functions provided by the system 200, such as those requested by applications executing on the first and second user devices 202, 211. In certain embodiments, the server 240 may include a memory 241 that includes instructions, and a processor 242 that executes the instructions from the memory 241 to perform various operations that are performed by the server 240. The processor 242 may be hardware, software, or a combination thereof. Similarly, the server 250 may include a memory 251 that includes instructions, and a processor 252 that executes the instructions from the memory 251 to perform the various operations that are performed by the server 250. In certain embodiments, the servers 240, 250, and 260 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 240, 250 may be communicatively linked to the communications network 235, any network, any device in the system 200, the pill pack 100, or any combination thereof.

The database 255 of the system 200 may be utilized to store and relay information that traverses the system 200, cache information and/or content that traverses the system 200, store data about each of the devices in the system 200, and perform any other typical functions of a database. In certain embodiments, the database 255 may store the output from any operation performed by the system 200 and/or pill pack 100, operations performed and/or outputted by any component, program, process, device, network of the system 200 and/or system 200, or any combination thereof. For example, the database 255 may store data from data sources, such as, but not limited to, the pill pack 100, the components of the pill pack 100, or a combination thereof. The database 255 may store information relating to the electrical signals monitoring by the pill pack 100, changes in electrical signals, information relating to detections of opened pill pouches, date and time information for opening a pill pouch, notifications relating to use of the pill pack 100, location information associated with the pill pack 100 and/or a user, alerts, information relating to compliance with a treatment regimen and/or compliance schedule, any other information, or a combination thereof. In certain embodiments, the database 255 may be connected to or reside within the communications network 235, any other network, or a combination thereof. In certain embodiments, the database 255 may serve as a central repository for any information associated with any of the devices and information associated with the system 200. Furthermore, the database 255 may include a processor and memory or be connected to a processor and memory to perform the various operations associated with the database 255. In certain embodiments, the database 255 may be connected to the servers 240, 250, 260, the first user device 202, the second user device 211, any devices in the system 200, any devices of the system 200, the pill pack 100, any other device, any network, or any combination thereof.

The database 255 may also store information obtained from the system 200, store information associated with the first and second users 201, 210, store location information for the first and second user devices 202, 211 and/or first and second users 201, 210, store user profiles associated with the first and second users 201, 210, store device profiles associated with any device in the system 200 and/or pill pack 100, store communications traversing the system 200, store user preferences, store demographic information for the first and second users 201, 210, store information associated with any device or signal in the system 200, store information relating to usage of applications accessed by the first and second user devices 202, 211, store any information obtained from any of the networks in the system 200, store historical data associated with the first and second users 201, 210, store device characteristics, store information relating to any devices associated with the first and second users 201, 210, or any combination thereof. The database 255 may store algorithms for analyzing data obtained from the pill pack 100, algorithms for determining compliance with a regimen, algorithms conducting artificial intelligence and/or machine learning, algorithms for comparing sensor data to baseline and/or threshold values, any other algorithms for performing any other calculations and/or operations in the system 200, or any combination thereof. The database 255 may also be configured to store information relating to detected conditions and/or events, actions to perform in response to the detected conditions and/or events, information indicating whether one or more of the actions have been performed, any other information provided by the system 200 and/or method 300, or any combination thereof. In certain embodiments, the database 255 may be configured to store any information generated and/or processed by the system 200, store any of the information disclosed for any of the operations and functions disclosed for the system 200 herewith, store any information traversing the system 200, or any combination thereof. Furthermore, the database 255 may be configured to process queries sent to it by any device in the system 200 and/or pill pack 100.

The system 200 may also include an external network 265. The external network 265 of the system 200 may be configured to link each of the devices in the system 200 to one another. For example, the external network 265 may be utilized by the first user device 202, the second user device 211, and/or the pill pack 200 to connect with other devices within or outside communications network 235. Additionally, the external network 265 may be configured to transmit, generate, and receive any information and data traversing the system 200. In certain embodiments, the external network 265 may include any number of servers, databases, or other componentry, and may be controlled by a service provider. The external network 265 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. In certain embodiments, the external network 265 may be outside the system 200 and may be configured to perform various functionality provided by the system 200, such as if the system 200 is overloaded and/or needs additional processing resources.

Notably, as shown in FIG. 2, the system 200 may perform any of the operative functions disclosed herein by utilizing the processing capabilities of server 260, the storage capacity of the database 255, or any other component of the system 200 to perform the operative functions disclosed herein. The server 260 may include one or more processors 262 that may be configured to process any of the various functions of the system 200. The processors 262 may be software, hardware, or a combination of hardware and software. Additionally, the server 260 may also include a memory 261, which stores instructions that the processors 262 may execute to perform various operations of the system 200. For example, the server 260 may assist in processing loads handled by the various devices in the system 200, such as, but not limited to, providing a pill pack having a pill disposed within one or more pill pouches and a membrane that covers the one or more pill pouches; monitoring circuits that covers a portion of a pill pouch for a change in an electrical signal; detecting that a pill pouch was opened based on changes in the electrical signals; recording the date and time that a pill pouch was opened; transmitting a signal indicating that a pill pouch was opened to a device; providing a geographic location that the pill pouch was opened; providing an alert to the mobile device if the location of the pill pack is greater than a predetermined distance from the mobile device; providing a compliance schedule; comparing the date and time information with the compliance schedule; generating notifications indicating whether compliance has been achieved or not; and performing any other suitable operations conducted in the system 200 or otherwise. In one embodiment, multiple servers 260 may be utilized to process the functions of the system 200. The server 260 and other devices in the system 200, may utilize the database 255 for storing data about the devices in the system 200 or any other information that is associated with the system 200. In one embodiment, multiple databases 255 may be utilized to store data in the system 200.

In certain embodiments, the system 200 may also include a computing device 270. The computing device 270 may include one or more processors 272 that may be configured to process any of the various functions of the system 200 and/or pill pack 100. The processors 272 may be software, hardware, or a combination of hardware and software. Additionally, the computing device 270 may also include a memory 271, which stores instructions that the processors 272 may execute to perform various operations of the system 200. For example, the computing device 270 may assist in processing loads handled by the various devices in the system 200, such as, but not limited to, devices and components of the pill pack 100.

Although the figures illustrate specific example configurations of the various components of the system 200, the system 200 may include any configuration of the components, which may include using a greater or lesser number of the components. For example, the system 200 is illustratively shown as including a first user device 202, a second user device 211, a communications network 235, a server 240, a server 250, a server 260, a database 255, and an external network 265. However, the system 200 may include multiple first user devices 202, multiple second user devices 211, multiple databases 225, multiple communications networks 235, multiple servers 240, multiple servers 250, multiple servers 260, multiple databases 255, multiple external networks 265, and/or any number of any of the other components inside or outside the system 200 and/or pill pack 100. Similarly, the system 200 may include any number of data sources, applications, systems, and/or programs. Notably, any of the components of the system 200 may be integrated into the pill pack 100 and vice versa. Furthermore, in certain embodiments, substantial portions of the functionality and operations of the system 200 may be performed by other networks and systems that may be connected to system 200.

Figure 3:
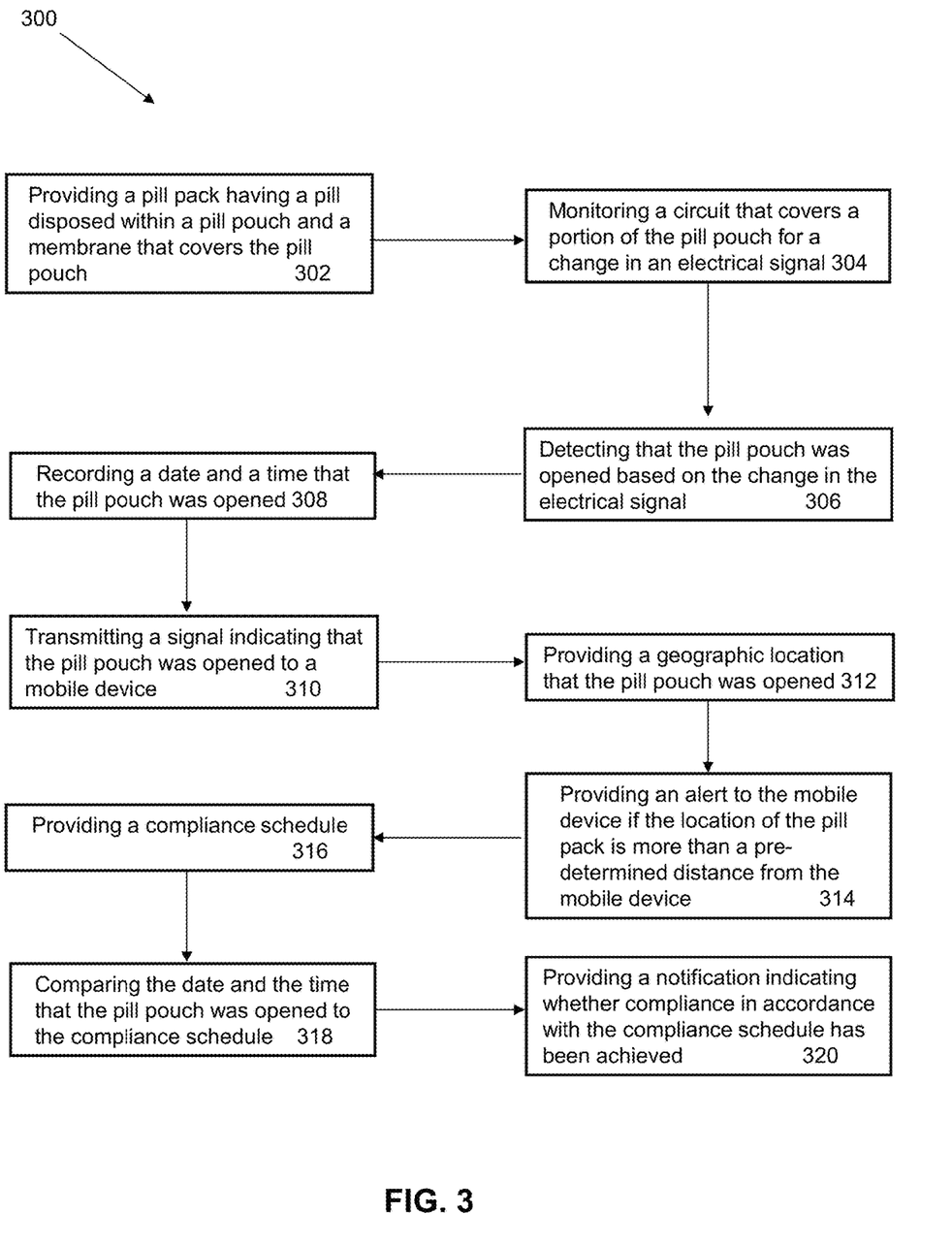
FIG. 3 is a flow diagram illustrating a sample method for utilizing a pill pack to monitor compliance with a regimen according to an embodiment of the present disclosure.

As shown in FIG. 3, an exemplary method 300 for monitoring compliance with a regimen by utilizing a pill pack 100 is schematically illustrated. The method 300 may include, at step 302, providing a pill pack 100 having a pill disposed within one or more pill pouches of the pill pack 100, and a membrane that covers the pill pouch. In certain embodiments, the providing may be performed and/or facilitated by utilizing any of the components of system 200, any other components, programs, devices, and/or individuals, or a combination thereof. At step 304, the method 300 may include monitoring a circuit that covers a portion of the pill pouch(es) for electrical signals and changes in electrical signals. In certain embodiments, the monitoring may be performed and/or facilitated by utilizing the pill pack 100, any of the components of system 200, the system 400, any other components, programs, devices, and/or individuals, or a combination thereof.

At step 306, the method 300 may include detecting that the pill pouch(es) was opened based on the change in the electrical signal detected. In certain embodiments, the detecting may be performed and/or facilitated by utilizing the pill pack 100, any of the components of system 200, the system 400, any other components, programs, devices, and/or individuals, or a combination thereof. At step 308, the method 300 may include recording a date and a time that the pill pouch(es) was opened. In certain embodiments, the recording may be performed and/or facilitated by utilizing the pill pack 100, any of the components of system 200, the system 400, any other components, programs, devices, and/or individuals, or a combination thereof. At step 310, the method 300 may include transmitting a signal to a mobile device (or other device) indicating that the pill pouch(es) was opened. In certain embodiments, the transmitting may be performed and/or facilitated by utilizing the pill pack 100, any of the components of system 200, the system 400, any other components, programs, devices, and/or individuals, or a combination thereof.

At step 312, the method 300 may include providing a geographic location that the pill pouch(es) was opened. In certain embodiments, the providing may be performed and/or facilitated by utilizing the pill pack 100, any of the components of system 200, the system 400, any other components, programs, devices, and/or individuals, or a combination thereof. At step 314, the method 300 may include providing an alert to the mobile device if the location of the opening of the pill pack 100 is more than a predetermined distance from the mobile device. In certain embodiments, the providing may be performed and/or facilitated by utilizing the pill pack 100, any of the components of system 200, the system 400, any other components, programs, devices, and/or individuals, or a combination thereof.

At step 316, the method 300 may include providing a compliance schedule. In certain embodiments, the providing may be performed and/or facilitated by utilizing the pill pack 100, any of the components of system 200, the system 400, any other components, programs, devices, and/or individuals, or a combination thereof. At step 318, the method 300 may include comparing the date and time that the pill pouch(es) was opened to the information in the compliance schedule/regiment. In certain embodiments, the comparing may be performed and/or facilitated by utilizing the pill pack 100, any of the components of system 200, the system 400, any other components, programs, devices, and/or individuals, or a combination thereof. At step 320, the method 300 may include providing a notification indicating whether compliance in accordance with the compliance schedule has been achieved. For example, if the date and time of the opening correspond with the instructions and/or directives in the compliance schedule, the notification will indicate compliance. However, if the time and time do not correspond with the instructions and/or directives in the compliance schedule, the notification will indicate lack of compliance. In certain embodiments, the providing may be performed and/or facilitated by utilizing the pill pack 100, any of the components of system 200, the system 400, any other components, programs, devices, and/or individuals, or a combination thereof.

Figure 4:
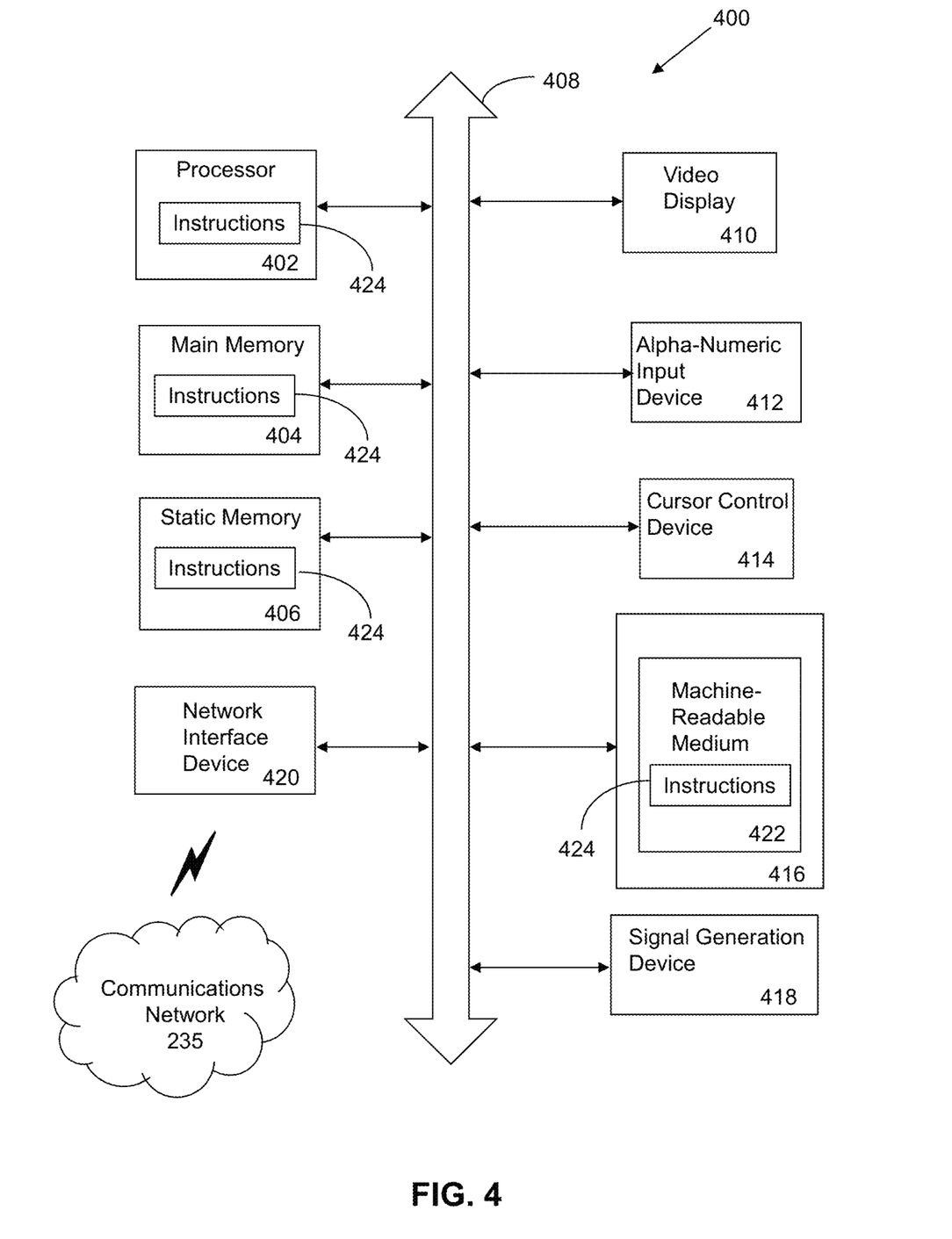
FIG. 4 is a schematic diagram of a machine in the form of a computer system within which a set of instructions, when executed, may cause the machine to perform any one or more of the methodologies or operations of the pill pack according to an embodiment of the present disclosure.

Referring now also to FIG. 4, at least a portion of the methodologies and techniques described with respect to the exemplary embodiments of the system 200 and pill pack 100 can incorporate a machine, such as, but not limited to, computer system 400, or other computing device within which a set of instructions, when executed, may cause the machine to perform any one or more of the methodologies or functions discussed above. The machine may be configured to facilitate various operations conducted by the system 200 and pill pack 100. For example, the machine may be configured to, but is not limited to, assist the system 200 by providing processing power to assist with processing loads experienced in the system 200, by providing storage capacity for storing instructions or data traversing the system 200, or by assisting with any other operations conducted by or within the system 200.

In some embodiments, the machine may operate as a standalone device. In some embodiments, the machine may be connected (e.g., using communications network 235, another network, or a combination thereof) to and assist with operations performed by other machines, programs, functions, and systems, such as, but not limited to, the first user device 202, the second user device 211, the server 240, the server 250, the database 255, the server 260, the external network 265, the communications network 235, the pill pack 100, any device, system, and/or program, or any combination thereof. The machine may be connected with any component in the system 200. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 400 may include a processor 402 (e.g., a central processing unit (CPU), a graphics processing unit (GPU, or both), a main memory 404 and a static memory 406, which communicate with each other via a bus 408. The computer system 400 may further include a video display unit 410, which may be, but is not limited to, a liquid crystal display (LCD), a flat panel, a solid state display, or a cathode ray tube (CRT). The computer system 400 may include an input device 412, such as, but not limited to, a keyboard, a cursor control device 414, such as, but not limited to, a mouse, a disk drive unit 416, a signal generation device 418, such as, but not limited to, a speaker or remote control, and a network interface device 420.

The disk drive unit 416 may include a machine-readable medium 422 on which is stored one or more sets of instructions 424, such as, but not limited to, software embodying any one or more of the methodologies or functions described herein, including those methods illustrated above. The instructions 424 may also reside, completely or at least partially, within the main memory 404, the static memory 406, or within the processor 402, or a combination thereof, during execution thereof by the computer system 400. The main memory 404 and the processor 402 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 422 containing instructions 424 so that a device connected to the communications network 235, the external network 265, another network, or a combination thereof, can send or receive voice, video or data, and communicate over the communications network 235, the external network 265, another network, or a combination thereof, using the instructions. The instructions 424 may further be transmitted or received over the communications network 235, the external network 265, another network, or a combination thereof, via the network interface device 220.

While the machine-readable medium 422 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

What is claimed is:

1. A pill package enclosure, comprising:
a membrane for covering one or more pill pouches in a pill pack; and
a circuit, wherein the circuit comprises a processor and a battery, and wherein a portion of the circuit covers a pill pouch of the pill pouches, wherein the portion of the circuit covering the pill pouch is coupled to the processor and the battery;
wherein the processor is configured to monitor a removal of a pill from the pill pouch by assessing changes in electrical signals from the portion of the circuit covering the pill pouch; and
wherein the processor is configured such that the removal of the pill from the pill pouch triggers a monitoring of a distance between the pill pack and a mobile device at a time corresponding to removal of the pill from the pill pouch.

2. The enclosure of claim 1, wherein the circuit is positioned on the membrane.

3. The enclosure of claim 1, wherein the circuit is positioned within the membrane.

4. The enclosure of claim 1, further comprising a wireless transmitter coupled to the processor.

5. The enclosure of claim 4, wherein the wireless transmitter is configured to wirelessly communicate with the mobile device and to create a unique identifier for the pill pack such that the pill pack is registered specifically to the mobile device.

6. The enclosure of claim 5, wherein the wireless transmitter is configured to send location information from the mobile device to the processor.

7. The enclosure of claim 5, wherein the processor is configured to identify the mobile device wirelessly communicating with the processor when the pill is removed from the pill pouch.

8. The enclosure of claim 1, further comprising:
a GPS receiver,
wherein the processor is configured to record a location of the enclosure using the GPS receiver when the pill is removed from the pill pouch.

9. A method for monitoring medication usage, the method comprising:
providing a pill pack having a pill disposed within a pill pouch and a membrane that covers the pill pouch;
monitoring a circuit that covers a portion of the pill pouch for a change in an electrical signal, wherein the change in the electrical signal occurs when the pill pouch is opened; and
recording a date and a time the pill pouch was opened by using a processor; and
initiating a detecting of a distance of the pill pack from a mobile device from when the pill pouch is opened.

10. The method of claim 9, further comprising transmitting a signal that a pill pouch was opened to the mobile device.

11. The method of claim 9, further comprising:
providing the geographic location where the pill pouch was opened by using a GPS receiver; and
recording the geographic location by using the processor.

12. The method of claim 9, further comprising:
providing a compliance schedule to the processor; and
comparing, by using the processor the date and the time when the pill pouch was opened with the compliance schedule.

13. The method of claim 9 further comprising:
using a GPS monitor to track a location of the pill pack; and providing an alert on a mobile device when the location of the pill pack is more than a pre-determined distance from the mobile device when the pill pouch was opened.

14. A monitored pill pack comprising:
a pill pack having a pill well;
a cover disposed on the pill well;
a circuit configured to monitor opening of the cover;
a processor configured to monitor a date and a time the cover is opened, the processor configured to monitor a distance between the pill pack and a mobile device when the cover is opened a wireless transmission device configured to transmit information recorded by the processor to the mobile device; and wherein the wireless transmission device is configured to transmit an alert to the mobile device when a location of the pill pack is more than a pre-determined distance from the mobile device when the cover is opened.

15. The monitored pill pack of claim 14, further comprising a GPS device.

16. The monitored pill pack of claim 14, further comprising a battery.

17. The monitored pill pack of claim 14, wherein the circuit is comprised of a flexible conductive material.

18. The monitored pill pack of claim 14, wherein the processor is configured to receive location information from the mobile device.

* * * * *